United States Patent
Belsom et al.

(10) Patent No.: US 9,429,510 B2
(45) Date of Patent: Aug. 30, 2016

(54) CORROSION SENSOR FOR INTERNAL STRUCTURE OF MACHINE

(71) Applicant: General Electric Company, Schenectady, NY (US)

(72) Inventors: Keith Cletus Belsom, Laurens, SC (US); Paul Stephen DiMascio, Greer, SC (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/543,989

(22) Filed: Nov. 18, 2014

(65) Prior Publication Data

US 2016/0139029 A1   May 19, 2016

(51) Int. Cl.
| | |
|---|---|
| *G01N 17/04* | (2006.01) |
| *G01N 25/00* | (2006.01) |
| *G01L 7/00* | (2006.01) |
| *G01N 27/00* | (2006.01) |

(52) U.S. Cl.
CPC ................. *G01N 17/04* (2013.01); *G01L 7/00* (2013.01); *G01N 25/00* (2013.01); *G01N 27/00* (2013.01)

(58) Field of Classification Search
CPC ...................................... G01N 17/04
See application file for complete search history.

(56) References Cited

U.S. PATENT DOCUMENTS

| | | | | |
|---|---|---|---|---|
| 5,039,228 | A | * | 8/1991 | Chalmers ................ G01M 7/00 374/141 |
| 8,475,110 | B2 | | 7/2013 | Hefner et al. |
| 8,643,389 | B2 | | 2/2014 | Hefner et al. |
| 2006/0101920 | A1 | * | 5/2006 | Carnal .................... G01N 17/04 73/706 |
| 2008/0282781 | A1 | * | 11/2008 | Hemblade ............ G01N 29/222 73/61.75 |
| 2009/0068060 | A1 | * | 3/2009 | Alfermann ............. G01N 17/04 422/53 |
| 2012/0103104 | A1 | * | 5/2012 | Butterfield ............... G01N 3/08 73/799 |

* cited by examiner

*Primary Examiner* — Jill Warden
*Assistant Examiner* — Matthew Krcha
(74) *Attorney, Agent, or Firm* — Ernest G. Cusick; Hoffman Warnick LLC

(57) ABSTRACT

A corrosion sensor for an internal structure of a machine is provided. The corrosion sensor may include a test cap having at least one of a material and a geometry configured to fail faster than a material of the internal structure due to a corrosive influence. A mount secures the test cap in position in an opening in a portion of the machine that defines an operational environment. A chamber is adjacent the test cap and in at least one of the test cap and the mount. A failure in the test cap creates an environmental change in the chamber that indicates exceeding a corrosion threshold and can be sensed by, for example, a temperature or pressure change.

19 Claims, 3 Drawing Sheets

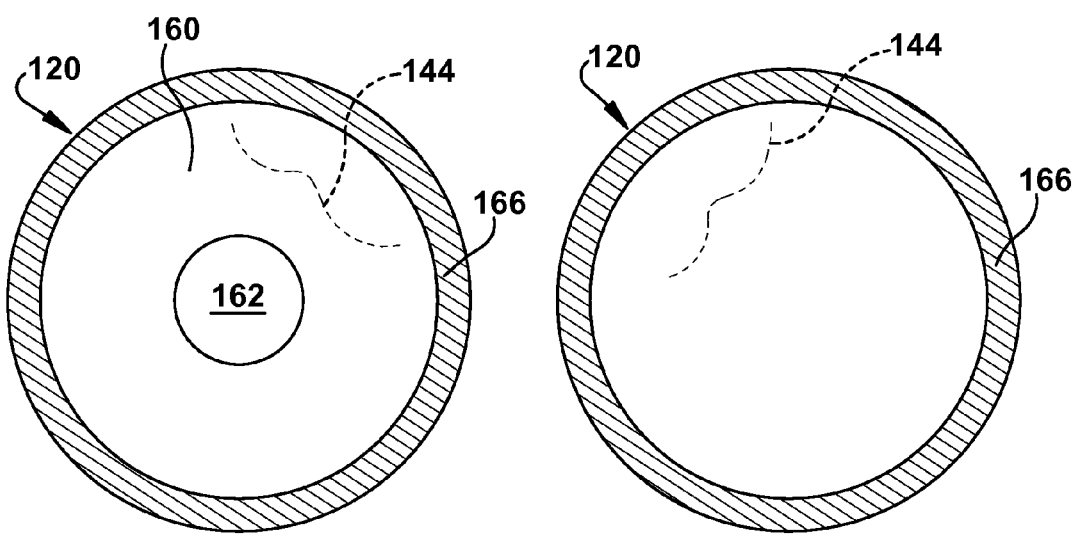

US 9,429,510 B2

CORROSION SENSOR FOR INTERNAL STRUCTURE OF MACHINE

BACKGROUND OF THE INVENTION

The disclosure relates generally to corrosion sensors, and more particularly, to a corrosion sensor for an internal structure of a machine such as a compressor.

Machinery and equipment operated in harsh environments are often subject to accelerated corrosion rates which, if not monitored or controlled, can result in premature aging and eventually failure of the machinery and equipment. For example, in a gas turbine, gases flow along a flow path in a compressor that compresses the gas flow. The compressor includes a number of internal structures such as blade airfoils and nozzles that may be subjects of corrosion. In particular, the constituents of air being compressed in the compressor can sometimes drive pitting creating corrosion and then initiating cracking due to the high stresses.

In some settings, corrosion sensors may be installed on metal surfaces other than the internal structure to monitor the presence and/or rate of any general corrosion. For example, a conventional corrosion sensor, which may be referred to as a 'coupon', may include a metal electrode similar to the metal requiring analysis or may include alternating layers of electrodes separated by dielectric material. In any event, the electrodes may have an oxidation potential comparable to that of the metal surfaces to which they are attached so that the general corrosion rate on the metal surfaces may be approximated by the general corrosion rate on the electrodes. Because conventional corrosion sensors are not stress loaded, they are not exposed to the mechanical and thermal loading, like the internal structures of concern. As a result, they are typically inaccurate to predict component failure. The only mechanism to forestall unforeseen down time in such settings is through periodic, visual inspections, which increases the down time.

BRIEF DESCRIPTION OF THE INVENTION

A first aspect of the disclosure provides a corrosion sensor for an internal structure of a machine, the corrosion sensor comprising: a test cap having at least one of a material and a geometry configured to fail faster than a material of the internal structure due to a corrosive influence; a mount to secure the test cap in position in an opening in a portion of the machine exposed to an operational environment at least similar to that of the internal structure; and a chamber adjacent the test cap and in at least one of the test cap and the mount, wherein an environmental change in the chamber caused by a failure of the test cap indicates exceeding a corrosion threshold.

A second aspect of the disclosure provides a corrosion sensor for an internal structure of a machine, the corrosion sensor comprising: a test cap having at least one of a material and a geometry configured to fail faster than a material of the internal structure due to a corrosive influence; a mount coupled to the test cap to threadably secure the test cap in position in an opening in a portion of the machine exposed to an operational environment at least similar to that of the internal structure; and a chamber adjacent the test cap and in at least one of the test cap and the mount, wherein an environmental change in the chamber caused by a failure of the test cap indicates exceeding a corrosion threshold, wherein the mount positions the test cap in the position such that the test cap is exposed to a stress greater than the internal structure.

The illustrative aspects of the present disclosure are designed to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which:

FIG. 3 shows a plan view from line A-A of FIG. 1 of the corrosion sensor of FIG. 1.

FIG. 4 shows a plan view from line B-B of FIG. 2 of the corrosion sensor of FIG. 2.

It is noted that the drawings of the disclosure are not to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

As indicated above, the disclosure provides a corrosion sensor for an internal structure of a machine. The internal structure for which the corrosion sensor is to indicate corrosion may include any element within an operational environment in the machine. An "operational environment" may include any internal, generally harsh surroundings within a machine that may also be exposed to stresses. Generally, the operational environment and the structure of the machine make it such that corrosion of the internal structure is not readily observable, thus requiring unnecessary down time to check for corrosion. A corrosion sensor as described herein provides a way to identify corrosion without unnecessary down time. For purposes of description, the corrosion sensor will be described relative to a gas turbine compressor. In this example, the internal structure may include, for example, an airfoil, a nozzle, portion of a casing, etc. It is emphasized that while the corrosion sensor will be described as applied to a gas turbine compressor, the teachings of the invention are applicable in a wide variety of machines that have internal structures that are exposed to a harsh environment and a wide variety of stresses. For example, other machines may include a gas turbine, a steam turbine, a combustor, heating/ventilation equipment, a pump, a compressor, a reciprocating engine, a gearbox, etc. Consequently, the variety of internal structures for which the corrosion sensor according to embodiments of the invention may be employed is vast.

Figure 1:
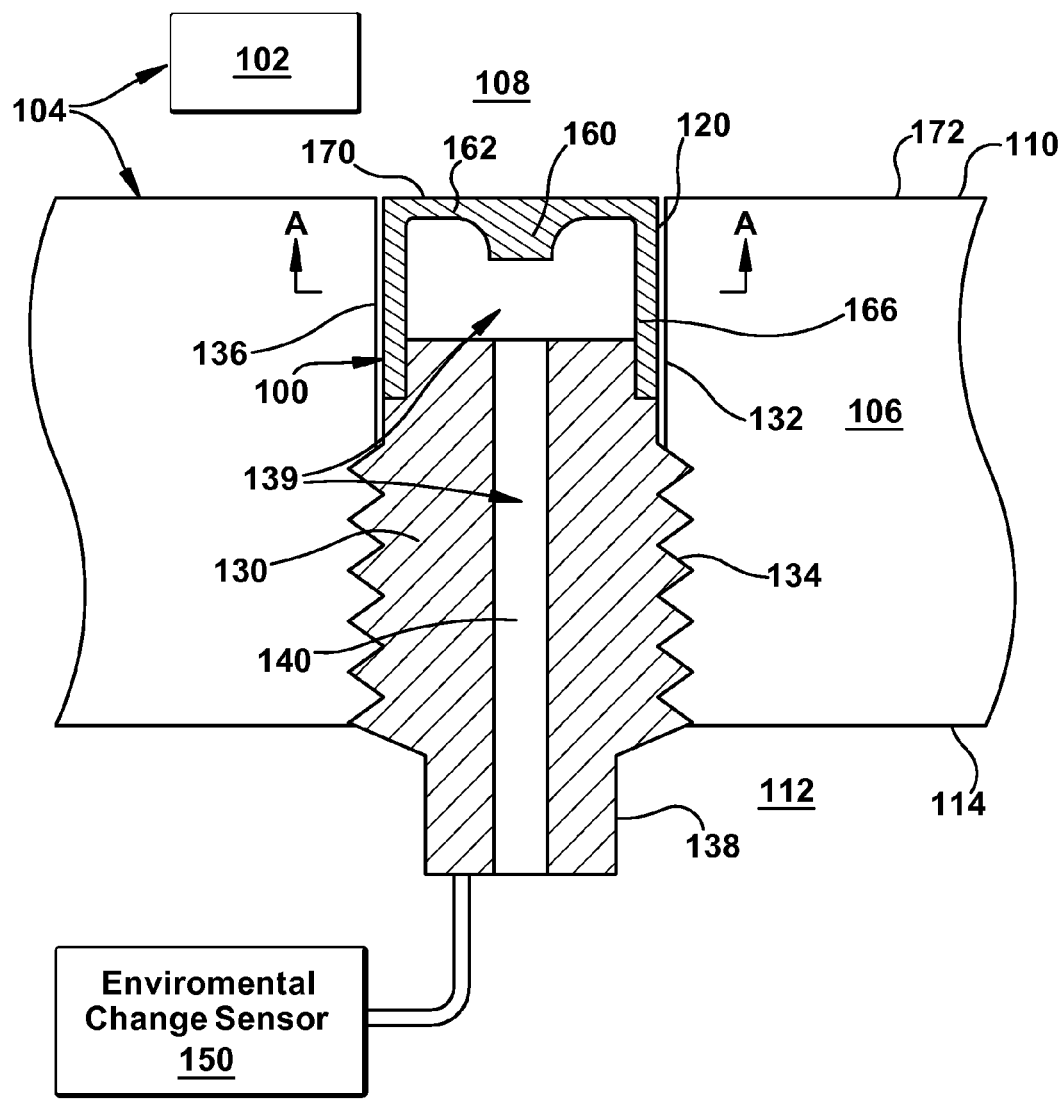
FIG. 1 shows a cross-sectional view of a corrosion sensor according to embodiments of the invention.

Referring to FIG. 1, a cross-sectional view of a corrosion sensor 100 according to embodiments of the invention is illustrated. As noted above, corrosion sensor 100 is illustrated as applied for an internal structure 102 (shown schematically for clarity) of a machine 104 in the form of a gas turbine compressor. Internal structure 102 may include, for example, an airfoil of the gas turbine compressor, which may be made of a material such as steel. Internal structure 102 could also be a stationary nozzle, a part of a casing, etc. Internal structure 102 may be a stationary and/or moving part of machine 104. The corrosion sensor 100 and machine 104 (such as a gas turbine compressor) with the internal structure 102 may comprise a corrosion sensor and gas turbine compressor system.

For purposes of description, corrosion sensor 100 has been illustrated as positioned in a casing 106 of the machine that defines or encloses an operational environment 108 on an internal side 110 of casing 106, and an area 112 having an environment, i.e., pressure, temperature, stress, etc., different than operational environment 106 sealed from operational environment 108. Area 112 may be external of a portion of the machine such as casing 106, or external of the entire machine 104, i.e., an atmospheric environment of the machine.

Corrosion sensor 100 may include a test cap 120 having at least one of a material and a geometry configured to fail faster than the material of internal structure 102 due to a corrosive influence. In particular, at least one of the material and geometry may be selected to create a predetermined time interval between failure of test cap 120 and failure of internal structure 102 based on an expected corrosion influence, e.g., a known working environment within machine 104 (temperature, pressure, operative fluids, etc). In one embodiment, test cap 120 material can be configured to fail faster than the material of internal structure 102 in a number of ways. In one example, where internal structure 102 includes an airfoil of a compressor made of a particular steel, test cap 120 may be made of the same steel or a material that will observe slightly faster corrosion than the particular steel. As an example, test cap 120 may be made of AISI 403 (Martensitic stainless steel Fe12Cr0.11C) which has less corrosion resistance than the airfoils made of GTD-450 (Precipitation hardened stainless steel Fe15.5Cr6.3Ni0.8Mo0.03C). In another example, test cap 120 may have a geometry such as size, shape, surface contour, surface roughness, angle of attack of working fluid, etc., configured to fail faster than internal structure 102. For example, test cap 102 may be slightly thinner than internal structure 102 so as to have higher stresses than the particular area of concern of internal structure 102. In this fashion, test cap 102 fails prior to the particular area of the internal structure. How much thinner test cap 120 is compared to internal structure 102 may be defined by a wide variety of factors such as but not limited to the material under investigation, the type of machine, the operational environment, how early of an indication of corrosion is desired, the material of casing 106, etc. In any event, test cap 120 is sized to ensure that it exhibits corrosion related failure created by the operational environment to which internal structure 102 is exposed earlier than the internal structure, e.g., a particular area of an airfoil. As may be described elsewhere herein, other materials and geometries may also be employed within the scope of the invention that provide faster failure of test cap 120 compared to internal structure 102.

Corrosion sensor 100 may also include a mount 130 securing test cap 120 in position in an opening 132 in a portion of the machine, e.g., casing 106, exposed to an operational environment 108 at least similar to (and preferably substantially identical to) that of internal structure 102. Mount 130 may be made of any suitable material capable of selective fixation within casing 106, e.g., metals such as steel, aluminum, nickel or alloys thereof, a hard plastic, etc. Casing 106 may be made of any material sufficient to stably position mount 130 and safely enclose operational environment 108, e.g., depending on the type of machine: metal, hard plastic, etc. Where necessary, mount 130 may be coupled to test cap 120 using any now known or later developed solution. In one embodiment, mount 130 is coupled to test cap 120 by brazing.

Figure 2:
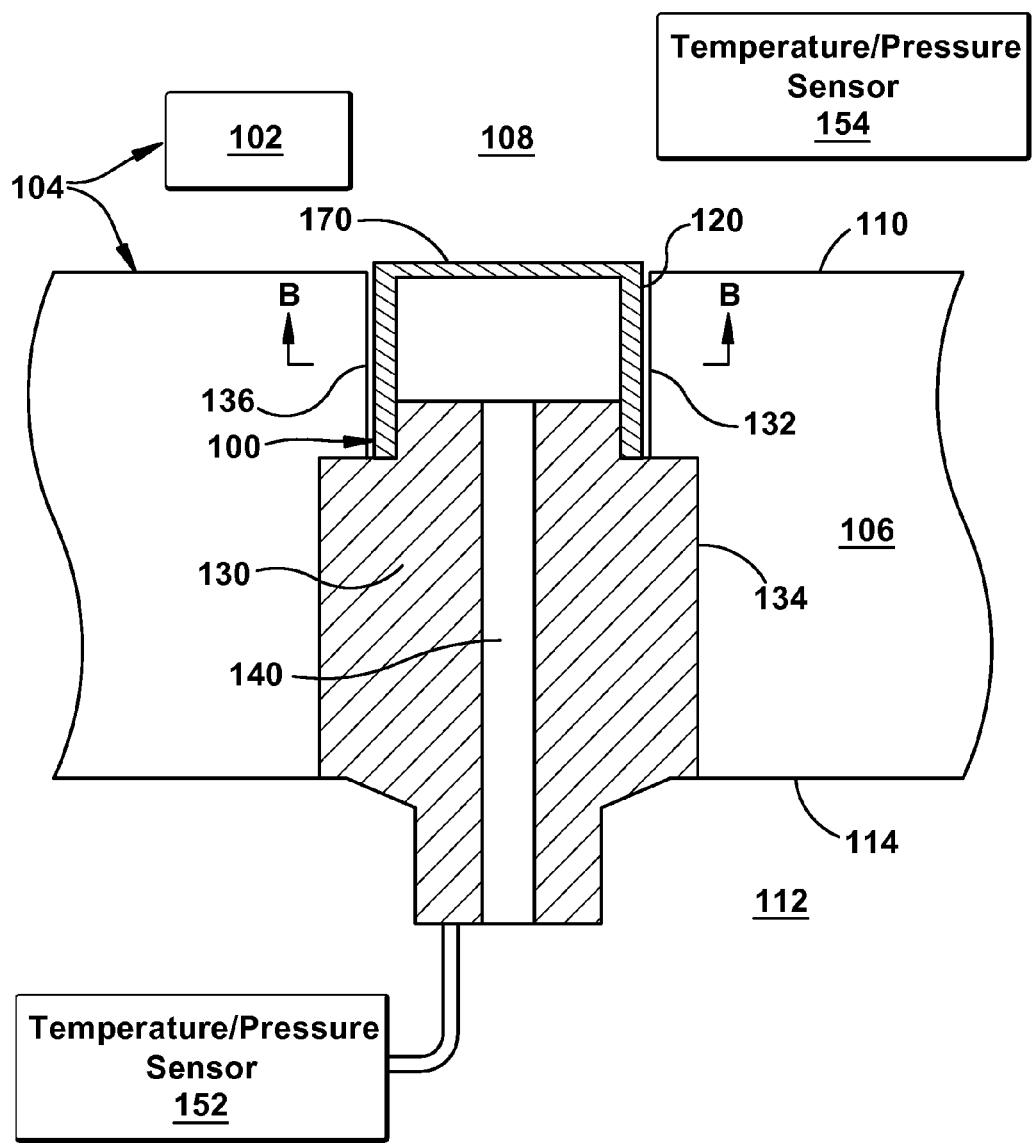
FIG. 2 shows a cross-sectional view of a corrosion sensor according to various alternative embodiments of the invention.

Mount 130 may couple test cap 120 in opening 132 in a number of fashions. In FIG. 1, mount 130 is threadably coupled in an external portion 134 of opening 132. In this case, an internal portion 136 of opening 132 is not threaded. In one example, opening 132 may take the form of an opening into which a borescope plug with a hex tightening feature would normally be positioned when the borescope is not in use. An external end 138 of mount 130 may include a tightening feature such as a hex head or similar feature so that mount 130 may be tightened into opening 132. FIG. 2 shows an alternative embodiment in which mount 130 may be, for example, welded or brazed in external portion 134 of opening 132, i.e., where mount 130 and test cap 120 include compatible materials. Here, internal portion 136 has a smaller diameter than external portion 134. As will be understood, a wide variety of mechanisms may be used to fix mount 130 in casing 106, and all are considered within the scope of the invention.

Mount 130 may also position test cap 120 in the position indicated such that the test cap is exposed to a stress greater than internal structure 102. For example, in one embodiment, opening 132 and, in particular, internal portion 136, may have a dimension smaller than test cap 120 such that the test cap is exposed to the stress greater than internal structure 102. For example, test cap 120 may be compressively stressed by an interference fit within internal portion 136 of opening 132 (i.e., no gaps as shown). A variety of other mechanisms may be employed to stress test cap 120 in a manner greater than internal structure 102 such that test cap 120 indicates corrosion earlier than internal structure 102. For example, one other way of providing a stress inducing load into a test cap 120 may include using a material with a different coefficient of thermal expansion that will cause higher stress when subject to the same temperature environment as internal part 102. Another example may include mounting corrosion sensor 100 onto an internal part 102 that is a moving structure of machine 104 such that loads created by the movement stress test cap 102. For example, internal structure 102 could be a rotating structure of machine 104 such that the centrifugal loads experienced by corrosion sensor 100 provide the stresses to test cap 120.

Returning to FIG. 1, corrosion sensor 100 also includes a chamber 139 adjacent test cap 120 and in at least one of test cap 120 and mount 130. As illustrated, mount 130 includes a bore 140 extending from test cap 120 to area 112 that forms part of chamber 139. In this example, collectively, bore 140 and an internal side of test cap 120 create chamber 139. It is understood that chamber 139 may be created in a number of alternative fashions such as solely by the internal side of test cap 120 or solely by bore 140, if one desires to manipulate the structural arrangement illustrated. In any event, an environmental change in chamber 139 caused by a failure of test cap 120 indicates exceeding of a corrosion threshold—indicating corrosion beyond an acceptable level is present. The "failure" of test cap 120 may take a variety of forms such as but not limited to a break or crack 144 (shown in FIGS. 3 and 4), a thinning, etc. Consequently, the environmental change in chamber 139 may also take a variety of forms, and a variety of environmental change sensor(s) 150 may be employed to sense the change. Where a break or crack occurs, the gases escaping from operational environment 108 may act to heat the gases within chamber 139 (e.g., within bore 140 and perhaps mount 130 itself) and/or may change the pressure within chamber 139. In some circumstances, a break or crack could also change a light intensity, e.g., emissivity, brightness, color or other light characteristic, within chamber 139. As will be described, the change in temperature, pressure, light intensity, etc., is detected by an environmental change sensor 150 (or sensors 152, 154) indicating the presence of a failure, and hence the exceeding of a corrosion threshold. More particularly, in one embodiment, environmental change sensor 150 may include a thermocouple operably coupled with chamber 139, i.e., such that a temperature within or on a surface of chamber 139 can be measured. In this case, a failure in test cap 120 indicative of exceeding a corrosion threshold may be indicated by a change in temperature measured by the thermocouple. The change in temperature can be caused, for example, by a thinning or break/crack of test cap 120. Any form of control system (not shown) may be employed with the thermocouple to ascertain the change in temperature. In an alternative embodiment, environmental change sensor 150 may include a pressure sensor operably coupled with chamber 139, i.e., such that a pressure within chamber 139 can be measured. Here, a failure in test cap 120 indicative of exceeding a corrosion threshold may be indicated by a change in pressure measured by pressure sensor 152 as caused, for example, by a thinning and/or break/crack in test cap 120. Again, any form of control system (not shown) may be employed with the pressure sensor to ascertain the change in pressure. Similarly, where a light intensity change occurs upon failure of test cap 120, environmental change sensor 150 may include any variety of photo-sensor capable of detecting the change. In another embodiment, environmental change sensor 150 may include an electric gauge that measures a selected electrical parameter across test cap 120. In this case, a failure in test cap 120 indicative of corrosion may be indicated by a change in the selected electrical parameter such as resistance, current, impedance measured by the electrical gauge. In an alternative embodiment, shown in FIG. 2, environmental change sensor 150 (FIG. 1) may be replaced by temperature or pressure sensors 152, 154 operatively coupled to bore 140 and within operational environment 108, respectively, such that a temperature or pressure within bore 140 and in operational environment 108 can both be determined and a comparison made to identify the failure in test cap 120. Regardless of the types of sensors used, in the event that test cap 120 receives adequate corrosion that it fails (e.g., cracks, opens, thins, etc.), environmental change sensor 150 (or sensors 152, 152) indicate the change indicative of corrosion so that corrective measures can be taken. While particular environmental change sensor types have been listed herein, a large variety of other sensors may be employed and are considered within the scope of the invention.

With further regard to test cap 120 geometry, a variety of other geometries (or shapes) may be employed that assist in ensuring exceeding the corrosion threshold when desired. The geometry may be selected to provide a greater or lesser time interval between the failure of the test cap and internal structure 102, e.g., by thickness of material, amount of exposed surface, stress created by shape, etc. In one embodiment, shown in cross-section in FIG. 1 and in a plan view in FIG. 3, test cap 120 may include a first portion 160 and a second portion 162. As seen best in FIG. 1, first portion 160 may have a thickness greater than second portion 162. In one embodiment, second, thinner portion 162 surrounds first, thicker portion 160; however, this is not necessary in all instances as the thicker portion can be non-concentrically located. First, thicker portion 160 may have any plan or cross-sectional shape desired to ensure corrosion indication. For example, first portion 160 may be circular in plan, and trapezoidal in cross-section. First portion 160 could also be substantially cylindrical so as to have a rectangular cross-section. In any event, a sidewall 166 may extend from portions 160, 162 to mate with mount 130. Sidewall 166 may be coupled to mount 130 in any fashion described herein. In this fashion, second portion 162 may endure a failure, e.g., a crack, indicating corrosion earlier than internal structure 102 (and first portion 160). In addition, portions 160, 162 may provide another mechanism to apply stress to test cap 120 greater than that applied to internal structure 102. For example, test cap 120 may be stiffened in its center by first portion 160 to provide radial "bellows" imparting tensile bending stress not applied to internal structure 102. In addition, portions 160, 162 may assist in maintaining test cap 120 from disintegrating or breaking such that part of it enters into the operational environment such that hit could cause additional damage. In an alternative embodiment, shown in cross-section in FIG. 2 and in a plan view in FIG. 4, where additional stress may be not be warranted by way of portions 160, 162, test cap 120 may have a substantially uniform thickness, i.e., with no portions 160, 162 having different thicknesses.

With further regard to the shape of test cap 120, as shown in FIGS. 1 and 2, test cap 120 may include a planar surface 170 exposed to operational environment 108. In an ideal situation, test cap 120 and planar surface 170 are exposed to operational environment 108 in the substantially same fashion as internal structure 102, e.g., angle of approach of a gas flow path, temperature, pressure, moisture, etc. In one example, planar surface 170 may be co-planar with an internal surface 110, 170 of the portion of the machine, e.g., casing 106, that defines operational environment 108. In an alternative embodiment, as shown in FIG. 2, planar surface 170 may extend into operational environment 108 beyond internal surface 110. It may also be desirable for planar surface 170 to be in a variety of other positions, e.g., slightly within internal surface 110 (not shown), angled, etc. Test cap 120 may also have a surface that is shaped to mimic internal structure 102, if desired. Although shown as having a substantially circular plan view shape, it is understood that test cap 120 and opening 132 need not be circular in all instances.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding internal structures, materials, acts, and equivalents of all means or step plus function elements in the claims below are intended to include any internal structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A corrosion sensor and gas turbine compressor system, the system comprising:
   a gas turbine compressor with an internal structure;
   a test cap having at least one of a material and a geometry configured to fail faster than a material of the internal structure due to a corrosive influence;
   a portion of the gas turbine compressor defining an opening and exposed to an operational environment at least similar to that of the internal structure;
   a mount to secure the test cap in position in the opening in the portion of the gas turbine compressor whereby the test cap is exposed to an operational environment at least similar to that of the internal structure; and
   a chamber adjacent the test cap and in at least one of the test cap and the mount,
   wherein an environmental change in the chamber caused by a failure of the test cap indicates exceeding a corrosion threshold.

2. The system of claim 1, wherein the test cap includes a first portion, a second portion, and a planar surface exposed to the operational environment, wherein the first portion has a thickness greater than the second portion.

3. The system of claim 2, wherein the second portion surrounds the first portion.

4. The system of claim 1, wherein the at least one of material and geometry is selected to create a predetermined time interval between failure of the test cap and failure of the internal structure based on an expected corrosion influence.

5. The system of claim 1, wherein the test cap includes a planar surface that is co-planar with an internal surface of the portion of the gas turbine compressor that defines the operational environment.

6. The system of claim 1, wherein the test cap and the mount are coupled by brazing.

7. The system of claim 1, further comprising an environmental change sensor configured to identify the environmental change indicative of exceeding the corrosion threshold.

8. The system of claim 7, wherein the environmental change sensor includes a thermocouple operably coupled with the chamber, wherein the environmental change includes a change in temperature measured by the thermocouple.

9. The system of claim 7, wherein the environmental change sensor includes a pressure sensor operably coupled with the chamber, wherein the environmental change includes a change in pressure measured by the pressure sensor.

10. The system of claim 7, wherein the environmental change sensor includes an electric gauge that measures a selected electrical parameter across the test cap, wherein the environmental change includes a change in the selected electrical parameter.

11. The system of claim 1, wherein the test cap has a dimension greater than a dimension of the opening in the portion of the gas turbine compressor to create an interference fit such that the test cap is exposed to a compression stress greater than the internal structure.

12. The system of claim 1, wherein the portion of the gas turbine compressor includes a threaded portion within the opening and the mount is threadably coupled in the opening.

13. A corrosion sensor and gas turbine compressor system, the system comprising:
   a gas turbine compressor with an internal structure;
   a test cap having at least one of a material and a geometry configured to fail faster than a material of the internal structure due to a corrosive influence;
   a portion of the gas turbine compressor exposed to an operational environment at least similar to that of the internal structure and defining an opening;
   a mount coupled to the test cap to threadably secure the test cap in position in the opening in the portion of the gas turbine compressor exposed to an operational environment at least similar to that of the internal structure; and
   a chamber adjacent the test cap and in at least one of the test cap and the mount,
   wherein an environmental change in the chamber caused by a failure of the test cap indicates exceeding a corrosion threshold,
   wherein the mount positions the test cap in the position such that the test cap is exposed to a stress greater than the internal structure.

14. The system of claim 13, wherein the test cap includes a first portion and a second portion, wherein the first portion has a thickness greater than the second portion and the second portion surrounds the first portion.

15. The system of claim 13, wherein the test cap includes a planar surface exposed to the operational environment, and the planar surface is co-planar with an internal surface of the portion of the gas turbine compressor that defines the operational environment.

16. The system of claim 13, further comprising an environmental change sensor configured to identify the environmental change indicative of exceeding the corrosion threshold.

17. The system of claim 16, wherein the environmental change sensor includes a thermocouple operably coupled with the chamber, wherein the environmental change includes a change in temperature measured by the thermocouple.

18. The system of claim 16, wherein the environmental change sensor includes a pressure sensor operably coupled with the chamber, wherein the environmental change includes a change in pressure measured by the pressure sensor.

19. The system of claim 16, wherein the environmental change sensor includes an electric gauge that measures a selected electrical parameter across the test cap, wherein the environmental change includes a change in the selected electrical parameter.

* * * * *